US007273616B2

(12) United States Patent
Chen et al.

(10) Patent No.: US 7,273,616 B2
(45) Date of Patent: Sep. 25, 2007

(54) **GENETICALLY ENGINEERED CELL LINES AND SYSTEMS FOR PROPAGATING *VARICELLA ZOSTER* VIRUS AND METHODS OF USE THEREOF**

(75) Inventors: Jason J. Chen, New York, NY (US); Anne A. Gershon, New York, NY (US); Zhenglun Zhu, Worcester, MA (US); Saul Silverstein, New York, NY (US); Michael D. Gershon, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 293 days.

(21) Appl. No.: 10/436,706

(22) Filed: May 12, 2003

(65) Prior Publication Data

US 2006/0121048 A1    Jun. 8, 2006

Related U.S. Application Data

(60) Provisional application No. 60/379,819, filed on May 10, 2002.

(51) Int. Cl.
*A61K 39/12* (2006.01)
(52) U.S. Cl. .............................. 424/204.1; 424/199.1; 435/91.1; 435/325; 435/235.1
(58) Field of Classification Search ............ 424/204.1, 424/199.1; 435/91.1, 325, 235.1
See application file for complete search history.

(56) References Cited

U.S. PATENT DOCUMENTS 6,302,685 B1 * 10/2001 Lobel et al. ................... 433/6

OTHER PUBLICATIONS

Morgan et al., "Insulin-like growth factor II receptor as a multifunctional binding protein," Nature, vol. 329, pp. 301-307. Sep. 24, 1987.
O'Gorman et al., "Decreased Insuline-like Growth Factor-II/Mannose 6-Phosphate Receptor Expression Enhances Tumorigenicity in JEG-3 Cells," Cancer Research, vol. 59, pp. 5692-5694. Nov. 15, 1999.
Pohlmann et al., "Cloning of a cDNA encoding the human cation-dependent mannose 6-phosphate-specific receptor," Proc. Natl. Acad. Sci. USA, vol. 84, pp. 5575-5579. Aug. 1987.
Arvin, A.M., et al., Humoral and cellular immunity to *Varicella-zoster* virus glycoprotein, gpI, and to a non-glycosulated protein p170, in strain 2 guinea pigs. J. Gen. Virol., 1987, 68: p. 2449-2454.
Cohen, J., et al., Chronic uveitis in guinea pigs infected with *Varicella-zoster* virus expressing *E. coli* beta-galactosidase. J. Infect. Dis., 1998, 177: p. 293-300.
Cohrs RJ., Barbour M. and Gilden DH., *Varicella-zoster* virus (VZV) transcription during latency in human ganglia: detection of transcripts mapping to genes 21, 29, 62 and 63 in a cDNA library enriched for VZV RNA. J. Virol. 1996 70(5): 2789-2796.

David, D.S., et al., Visceral *Varicella-zoster* after bone marrow transplantation: report of a case series and review of the literature. Am. J. Gasteroenterol., 1998, 93: p. 810-813.
Fiorica-Howells, E., Wade, P.R. and Gershon, M.D., Serotonin-induced increase in cAMP in ganglia isolated from the myenteric plexus of the guinea pig small intestine: mediation by a novel 5-HT receptor. Synapse, 1993, 13: p. 333-349.
Furness, J. B., et al., Intrinsic primary afferent neurons of the intestine. Prog. Neurobiol., 1998, 54(1): p. 1-18.
Gershon, M.D., Kirchgessner, A.L. and Wade, P.R., Functional anatomy of the enteric nervous system, in Physiology of the gastrointestinal tract. Third Edition, Johnson, L.R., et al., Editors. 1994, Raven Press: New York. p. 381-422.
Gilden, D.H., et al., Neurologic complications of the reactivation of *Varicella-zoster* virus. N. Engl. J. Med., 2000. 342: p. 635-645.
Kennedy, P., Grinfield, E. and Gow, J.W., Latent *Varicella-zoster* virus in human dorsal root ganglia. Virology, 1999, 258: p. 451-454.
Kennedy PG., Grinfeld E. and Gow, J.W., Latent *Varicella-zoster* virus is located predominantly in neuron in human trigeminal ganglia. Proc Natl Acad Sci USA 1998 95(8): 4658-4662.
Kennedy PG., Grinfeld E. and Bell JE., *Varicella-zoster* virus gene expression in latently infected and explanted human ganglia. J. Virol. 2000 74(24): 11893-11898.
Kirchgessner, A.L., Tamir, H and Gershon, M.D., Identification and stimulation by serotonin of intrinsic sensory neurons of the submucosal plexus of the guinea pig gut: activity-induced expression of Fos immunoreactivity. J. Neurosci., 1992, 12: p. 235-249.
Kinchington PR., Fite K. and Turse SE., Nuclear accumulation of IE 62, the *Varicella-zoster* virus (VZV) major transcriptional regulatory protein, is inhibited by phosphorylation mediated by the VZV open reading fram 66 protein kinase. J. Virol. 2000, 74(5): 2265-2277.
Kunze, W.A.A. and Furness, J.B., The enteric nervous system and regulation of intestinal motility. Annu. Rev. Physiol., 1999, 61: p. 117-142.
Kunze, W. A., Bornstein, J.C. and Furness, J.B., Identification of sensory nerve cells in a peripheral organ (the intestine) of a mammal. Neuroscience, 1995, 66: p. 1-4.
Lowry, P. W., et al., Immunity in strain 2 guinea pigs inoculated with vaccinia virus recombinants expressing *Varicella-zoster* virus glycoproteins I, IV,V, or the protein product of the immediate early gene 62. J. Gen Virol, 73: p. 811-819.
Lowry, P. W., et al., Investigation of the pathogenesis of *Varicella-zoster* virus infection in guinea pigs by using polymerase chain reaction. J. Infect. Dis., 1993, 167: p. 78-83.

(Continued)

*Primary Examiner*—Ali R. Salimi
(74) *Attorney, Agent, or Firm*—Wilmer Cutler Pickering Hale and Dorr LLP

(57) ABSTRACT

The present invention provides genetically engineered cell lines, recombinant vectors, and vaccines. The present invention also provides methods for generating an in vitro system for Varicella zoster virus (VZV), and the in vitro systems generated by these methods. The present invention further provides methods for reactivating VZV, and VZV reactivated by these methods. Finally, the present invention provides a method of screening for an agent for treating VZV infection.

3 Claims, 25 Drawing Sheets

OTHER PUBLICATIONS

Lungu, O. and Annunziato, P., VZV: Latency and reactivation, in Contributions to microbiology: *Varicella-zoster* virus: molecular biology, pathogenesis, and clinical aspects, Wolff, M.H., Schunemann, W. and Schmidt, A., Editors. 1999, Karger: Basel. p. 61-75.

Lungu O., et al., Aberrant intracellular localization of *Varicella-zoster* virus regulatory proteins during latency. Proc Natl Acad Sci USA 1998, 95(12): 7080-7085.

Matsunaga Y., Yamanishi K. and Takahashi M., Experimental infection and immune response of guinea pigs with *Varicella-zoster* virus. Infect Immun. 1982, 37(2): p. 407-412.

Myers, M., Duer, H.L. and Haulser, C.K., Experimental infection of guinea pigs with *Varicella-zoster* virus. J. Infect Dis, 1980, 142: p. 414-420.

Myers, M., Stanberry, L. and Edmond, B., *Varicella-zoster* virus infection of strain 2 guinea pigs. J. Infect Dis, 1985, 151: p. 106-113.

Myers, M.G., Connelly, B and Stanberry, L.R., Varicella in hairless guinea pigs. J. Infect Dis, 1991, 163:p. 746-751.

Myers, M. and Stanberry, L., Drug testing for activity against *Varicella-zoster* virus in hairless guinea pigs. Antiviral Res., 1991, 15: p. 341-344.

Pan, H. and Gershon MD., Activation of intrinsic afferent pathways in submucosal ganglia of the guinea pig small intestine. J. Neurosci. 2000, 20(9): 3295-3309.

Pompolo, S. and Furness, J.B., Ultrastructure and synaptic relationships of calbindin-reactive, Dogiel type II neurons, in the myenteric ganglia of guinea-pig small intestine. J. Neurocytol., 1988. 17:p. 771-782.

Pui, J.C., et al., Demonstration of *Varicella-zoster* virus infection in the muscularis propria and myenteric plexi of the colon in an HIV-positive patient with herpes zoster and small bowel pseudo-obstruction (Ogilivie's syndrome). Am. J. Gastroenterol., 2001, 96(5): p. 1627-1630.

Rogers, S. Y., Irving, W. and Russell, N.H., Visceral *Varicella zoster* infection after bone marrow transplantation without skin involvement and the use of PCR for diagnosis. Bone Marrow Transpl., 1995. 15: p. 805-807.

Sabella, C., et al., Immunization with the immediate-early tegument protein (open reading frame 62) of *Varicella-zoster* protects guinea pigs against virus challenge. J. Virol. 1993, 67(12): 7673-7676.

Sato, H., et al., Immune response to *Varicella-zoster* virus glycoproteins in guinea pigs infected with Oka varicella vaccine. Vaccine, 1998, 16: p. 1263-1269.

Schafer, K. H., et al., A new method for the isolation of myenteric plexus from the newborn rat gastrointestinal tract. Brain Res Protoc, 1997, 1(2): p. 109-113.

Schiller, G. L., et al., Abdominal presentation of *Varicella-zoster* infection in recipients of allogenetic bone marrow transplantation Bone Marrow Transpl., 1991, 7: p. 489-491.

Stemmer, S. M., et al., Fatal noncutaneous visceral infection with *Varicella-zoster* virus in a patent with lymphoma after autologous bone marrow transplantation. Clin Infect Dis, 1993, 16: p. 497-499.

Takahashi, M., et al., Live vaccine used to prevent the spread of varicella in children in hospital. Lancet, 1974, 2: p. 1288-1290.

Tribble, D. R., Church, P. and Frame, J. N., Gastrointestinal visceral motor complications of dermatomal herpes zoster: report of 2 cases and a review Clin. Infect. Dis, 1993, 17: p. 431-436.

Xia, Y., Fertel, R.H. and Wood, J.D., Stimulation of formation of cAMP by 5-hydroxytryptamine in myenteric ganglia isolated from guinea pig small intestine. Life Sci., 1994, 55: p. 685-692.

Zhai J., et al., Inward currents in neurons from newborn guinea pig intestin: mediation by 5-hydroxytryptamine type 3 receptors. J. Pharmacol Exp. Ther. 1999, 291 (1): 374-382.

* cited by examiner

Fig. 3 Intracellular transport of VZV

MPRs direct newly assembled VZV to late endosomes

- VZV accumulates in late endosomes.
- MPRs traffic to late endosomes.
- Late endosomes contain the immunoreactivities of VZV gE and MPRs.
  - *Late endosomes are acidic and degrade VZV prior to exocytosis.*

Fig. 4

HELF infection by cell-free VZV is inhibited by phosphorylated sugars

- Man 6-P inhibits infection of HELF by VZV.
  - Concentration-dependent.
  - Man 6-P > Glu 6-P > Glu 1-P.
  - Order of potency = binding to MPRs.

- *These data suggest that MPRs play a role in the infection of cells by VZV.*

Fig. 6

Downregulation of MPR$^{ci}$s inhibits infection by cell-free VZV

- MPR$^{ci}$-KO cells contain little MPR immunoreactivity (A, B).
- KO-MeWo cells are resistant to infection by cell-free VZV (C, D).

Fig. 8

MPR$^{ci}$-KO cells can be infected by cell-associated VZV.

VZV spreads between infected cells *in vitro* by fusion, which is independent of the viral envelope and thus also of MPR$^{ci}$s.

Fig. 9

MPR$^{ci}$-KO cells release infectious VZV into the culture supernatant.

- The supernatant from cultures of infected wild-type MeWo cells cannot pass VZV infection to target HELF cells (A and B).

- The supernatant from infected MPR$^{ci}$-KO cell cultures passes VZV infection to target HELF cells (C and D).

Fig. 10

VZV nucleocapsids assemble in the nuclei of infected KO-MeWo cells

- KO-MeWo cells were infected with cell-associated VZV.
- Intial stage of nucleocapsid assembly is similar to that seen in other cells.

Fig. 11

Enveloped VZV enters the perinuclear cisterna of KO-MeWo cells

- Tegument is lacking in the enveloped virions.
- Unenveloped nucleocapsids enter the cytosol.

Fig. 12

In KO-MeWo cells transport vesicles contain individual virions

- Post-TGN VZV is transported individually in vesicles.
- VZV does not accumulate in late endosomes.

Fig. 13

Expression of HSV ICP0 causes VZV to reactivate in enteric neurons

- Enteric neurons were latently infected with VZV.
- ICP0 was introduced in an adenoviral vector.
  - ICP0 is the HSV homologue of VZV ORF61.

*ICP0 appears to complement ORF61.*

Fig. 18

Infected ganglia contain mRNA and DNA encoding VZV proteins.

| ORF | cRNA (1 wk) | cRNA (2 wks) | cDNA (1 wk) | cDNA (2 wks) |
|---|---|---|---|---|
| 4 | ++++ | +++ | ++++ | +++ |
| •14 (gC) | •none | •none | •+++ | •+ |
| 21 | ++ | +++ | ++++ | ++ |
| 29 | +++ | ++ | ++++ | +++ |
| 40 | +++ | ++ | ++++ | +++ |
| 62 | ++ | ++ | +++ | ++ |
| 63 | ++ | + | +++ | ++ |
| •68 (gE) | •none | •none | •++ | •+ |

GENETICALLY ENGINEERED CELL LINES AND SYSTEMS FOR PROPAGATING *VARICELLA ZOSTER* VIRUS AND METHODS OF USE THEREOF

RELATED APPLICATION

This application claims the benefit of U.S. Provisional Application No. 60/379,819, filed May 10, 2002.

BACKGROUND OF THE INVENTION

*Varicella zoster* virus (VZV) is the cause of chickenpox (varicella) and shingles (zoster). Varicella is a primary infection in which VZV infects a naïve host. Zoster is the result of the reactivation of VZV, which has remained latent in its host, often for many years. A major paradox has impeded research on VZV for many years: VZV is highly infectious and spreads readily from an infected host to susceptible individuals, yet, it is extremely difficult to propagate in vitro, because it spreads only by direct cell-to-cell contact when it is grown in tissue culture. The dissemination of VZV among a population of susceptible subjects is mediated by cell-free virions, which are thought to be airborne. Cell-to-cell spread of VZV in vitro does not depend on cell-free virions, which are not released in viable form by infected cells in tissue culture. Instead, cells that are infected in vitro fuse with their uninfected neighbors enabling infection to be transferred intracellularly.

SUMMARY OF THE INVENTION

The present invention provides a genetically engineered cell line stably transformed with a nucleotide sequence encoding at least two full-length mannose-6-phosphate receptors.

Additionally, the present invention provides a genetically engineered cell line stably transformed with a nucleotide sequence encoding a full-length mannose-6-phosphate receptor and a full-length insulin-like growth factor receptor.

Also provided is a recombinant vector comprising a nucleotide sequence encoding at least two full-length mannose-6-phosphate receptors.

The present invention further provides a vaccine comprising an attenuated live virus produced by culturing genetically-engineered cells stably transformed with a nucleotide sequence encoding at least two full-length mannose-6-phosphate receptors and a pharmaceutically acceptable carrier.

The present invention is also directed to a method for generating an in vitro system for *Varicella zoster* virus (VZV), by: (a) isolating enteric ganglia from guinea pig; and (b) contacting the enteric ganglia with cell-free VZV to generate latent expression of the VZV. Also provided is an in vitro system for VZV generated by this method.

The present invention further provides an in vitro system for *Varicella zoster* virus (VZV), comprising an enteric ganglion that has been contacted with cell-free VZV to produce a latent VZV, wherein the VZV is subsequently reactivated to express VZV in an active form.

Additionally, the present invention provides a method for reactivating *Varicella zoster* virus (VZV), by: (a) isolating enteric ganglia from guinea pig; (b) contacting the enteric ganglia with cell-free VZV to generate latent expression of the VZV; and (c) contacting the infected ganglia with a vector containing a nucleic acid sequence encoding VZV ORF61 or a homologue thereof. Also provided is a *Varicella zoster* virus reactivated by this method.

Finally, the present invention provides a method of screening for an agent for treating *Varicella zoster* virus (VZV) infection, comprising use of an in vitro system for VZV, wherein the in vitro system comprises an enteric ganglion that has been contacted with cell-free VZV to produce a latent VZV, and wherein the VZV is subsequently reactivated to express VZV in an active form.

Additional aspects of the present invention will be apparent in view of the description which follows.

BRIEF DESCRIPTION OF THE FIGURES

FIG. 4 illustrates that MPRs direct newly assembled VZV to late endosomes;

FIG. 6 demonstrates that human embryonic lung cells (HELF) infection by cell-free VZV is inhibited by phosphorylated sugars;

FIG. 8 shows that downregulation of $MPR^{ci}$s inhibits infection by cell-free VZV;

FIG. 9 demonstrates that $MPR^{ci}$-KO (knock-out) cells can be infected by cell-associated VZV;

FIG. 10 illustrates that $MPR^{ci}$-KO cells release infectious VZV into the culture supernatant;

FIG. 11 illustrates that VZV nucleocapsids assemble in the nuclei of infected KO-MeWo cells;

FIG. 12 shows that enveloped VZV enters the perinuclear cisterna of KO-MeWo cells;

FIG. 13 demonstrates that, in KO-MeWo cells, transport vesicles contain individual virions;

FIG. 18 demonstrates that expression of HSV ICP0 causes VZV to reactivate in enteric neurons;

FIG. 22 shows that infected ganglia contain mRNA and DNA encoding VZV proteins;

DETAILED DESCRIPTION OF THE INVENTION

Figure 1:
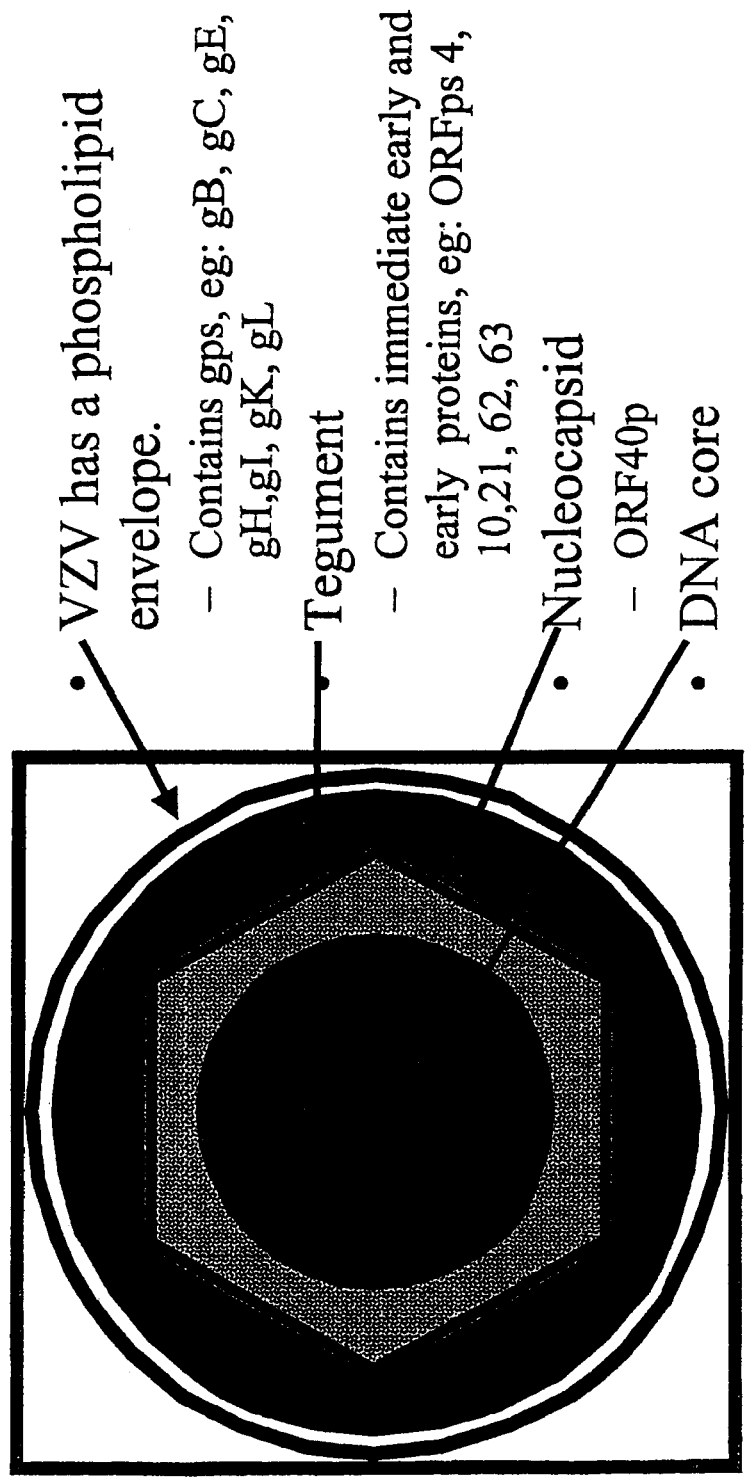
FIG. 1 is an illustration of a *Varicella Zoster* Virus (VZV) particle.

The inventors have demonstrated that viable VZV is not released to the medium by cultured cells because newly assembled virions are diverted from the secretory pathway to late endosomes where they encounter an acidic environment and lysosomal enzymes. The viral particles are then degraded in these endosomes before the virions are released to the medium by exocytosis. Only degraded VZV, which is not infectious, thus is delivered to the extracellular medium. VZV receives its final envelope in the trans-Golgi network (TGN). This cellular organelle is an intracellular sorting location and is the site where lysosomal enzymes are separated from proteins destined to be secreted. Diversion of lysosomal enzymes occurs because they contain mannose-6-phosphate (Man 6-P) groups that enable them to bind to mannose-6-phosphate receptors (MPRs), which are responsible for routing the lysosomal enzymes to endosomes. There are 2 MPRs, a large cation-independent molecule, which is also the receptor for insulin-like growth factor 2 (Man 6-P/IGF2R), and a small cation-dependent molecule. Lysosomal enzymes dissociate from MPRs in endosomes and are transported within the interiors of vesicles to lysosomes, while the MPRs are transported in membranes either back to the TGN or to the plasma membrane. The Man 6-P/IGF2Rs in the plasma membrane are able to bind to extracellular molecules that express Man 6-P groups, such as those of lysosomal enzymes, and mediate the endocytosis of these ligands.

The inventors surprisingly found that newly assembled VZV is diverted from the secretory pathway of infected cells by Man 6-P/IGF2Rs, which is thus responsible for the delivery of enveloped virions to endosomes. This is supported by observations that glycoproteins of the VZV envelope contain Man 6-P groups. In addition, the simple addition of Man 6-P to the medium in which cells are growing prevents these cells from becoming infected by cell-free VZV. Man 6-P interferes with the interaction between plasma membrane Man 6-P/IGF2R and the Man 6-P groups of extracellular molecules. Man 6-P does not prevent the cell-to-cell spread of VZV in vitro, which because it depends on the fusion of adjacent cells, which is independent of the interaction of viral Man 6-P with Man 6-P/IGF2R. These observations suggest that the Man 6-P groups of the glycoproteins of the VZV envelope interact with cellular Man 6-P/IGF2Rs and thus play critical roles in the ability of cell-free VZV to infect target cells and in the transport within infected cells of newly assembled VZV from the TGN to endosomes.

Accordingly, the inventors produced a cell line that is deficient in Man 6-P/IGF2R. Because of the strong preference of VZV for human cells, the Man 6-P/IGF2R-deficient cell line was derived from MeWo cells, a human melanoma tumor cell line, which is known to be susceptible to infection by VZV and to support the growth of VZV in vitro.

The Man 6-P/IGF2R-deficient MeWo cells were found to be far more resistant to infection by cell-free VZV than their parental control MeWo cells; however, infected cells can transfer VZV infection to the Man 6-P/IGF2R-deficient MeWo cells as readily as to the parental control MeWo cells. The medium in which parental control MeWo cells is growing is not infectious and cannot be used to transfer infection with VZV to susceptible target cells (human embryonic lung cells [HELF] are employed as the susceptible targets). In contrast, the medium in which Man 6-P/IGF2R-deficient MeWo cells is growing does contain infectious VZV and can be used to transfer infection with VZV to target HELF cells. This is the first cell line that, when infected with VZV, releases substantial quantities of infectious VZV particles to the ambient medium. The medium in which the Man 6-P/IGF2R-deficient MeWo cells are growing is thus extraordinarily useful as a source of intact, non-degraded, infectious VZV. The resistance of the Man 6-P/IGF2R-deficient MeWo cells to infection by cell-free VZV confirms that the Man 6-P/IGF2R plays an important role in enabling VZV to enter target cells. Infection of Man 6-P/IGF2R-deficient MeWo cells must be accomplished by adding other infected cells to them. The infected cells can thus infect the Man 6-P/IGF2R-deficient MeWo cells by cell-to-cell contact, which is Man 6-P/IGF2R-independent.

The successful maintenance and easy use of the Man 6-P/IGF2R-deficient MeWo cells depends on the knockdown of the Man 6-P/IGF2R being incomplete. When the Man 6-P/IGF2R expression is abolished, the resulting cells grow poorly and slowly. The current Man 6-P/IGF2R-deficient MeWo cells express small amounts of the Man 6-P/IGF2R and thus grow adequately, can be maintained without excess difficulty, yet still release infectious VZV.

Uses of the Man 6-P/IGF2R-deficient MeWo cells include the development of new and reliable methods to produce the VZV vaccine. This vaccine is an attenuated live virus that must be produced by cultured cells. It grows in culture, like wild-type VZV, only by cell-to-cell contact. The final product has to be liberated from the small intracellular compartment that contains newly assembled virions that have not yet been transported to endosomes. Virions that have been degraded in endosomes are useless as components of the vaccine. Yields of live virus are thus very low. Propagation in the Man 6-P/IGF2R-deficient MeWo cells should produce high yields of much more readily purified viable virus. In addition to being extremely useful in vaccine production, the Man 6-P/IGF2R-deficient MeWo cells should be just as helpful in developing new strains of VZV for future vaccines. Finally, the virus produced in Man 6-P/IGF2R-deficient MeWo cells is likely to be much more uniform and readily controlled than that produced in ordinary tissue culture cells. The non-controllable degradation of virions is avoided, yields are improved, and a step of cell lysis can be avoided in vaccine production. Contamination of the vaccine with cellular constituents and other viruses that might be contained in tissue culture cells can also be minimized.

The Man 6-P/IGF2R-deficient MeWo cells will also help in research on VZV itself. As such, Man 6-P/IGF2R-deficient MeWo cells will be of great value and sought after by research workers hoping to develop antiviral drugs and those seeking to understand the basic properties of VZV. Although the Man 6-P/IGF2R has been most strongly implicated as important, as described in the biology of VZV, the receptor may also play roles in the biology of other related herpesviruses, such as herpes simplex virus types 1 and 2 and pseudorabies virus. These virions do spread through media in vitro, but they may well spread more readily when propagated in Man 6-P/IGF2R-deficient MeWo cells. The Man 6-P/IGF2R-deficient MeWo cells, finally, are likely to be attractive to cell biologists who are interested in the basic properties of lysosomes, endosomes, receptor-mediated endocytosis, autophagy, and the pathogenesis of lysosomal storage disease.

The present invention is described in the following Examples, which are set forth to aid in the understanding of the invention, and should not be construed to limit in any way the scope of the invention as defined in the claims which follow thereafter.

EXAMPLES

Example 1

Production of Man 6-P/IGF2R-Deficient Cells

The deficient expression of Man 6-P/IGF2Rs was induced by stably transfecting parent MeWo cells (available from the European Collection of Cell Cultures (ECACC) Salisbury, Wiltshire) with cDNA encoding the full-length Man 6-P/IGF2R in the antisense configuration. The cDNA construct was packaged in a retroviral vector that also contained a puromycin resistance gene. The cells that were infected by the vector, and thus expressed mRNA encoding the Man 6-P/IGF2R in the antisense configuration, was selected in media containing puromycin. The success of the knockdown of the Man 6-P/IGF2R was confirmed by Western analysis and by immunocytochemistry; both techniques demonstrated reduced Man 6-P/IGF2R expression. In addition, the Man 6-P/IGF2R-deficient MeWo cells were found to contain less cathepsin D (a lysosomal enzyme that was investigated as a marker) than control parental MeWo cells. This demonstration was again accomplished by Western analysis and by immunocytochemistry. The Man 6-P/IGF2R-deficient cells also secreted a greater amount of another lysosomal enzyme, acid phosphatase, than parental MeWo cells (shown by direct measurement of acid phosphatase activity in cells and in media and by Western analyses of media and cell lysates).

Figure 2:
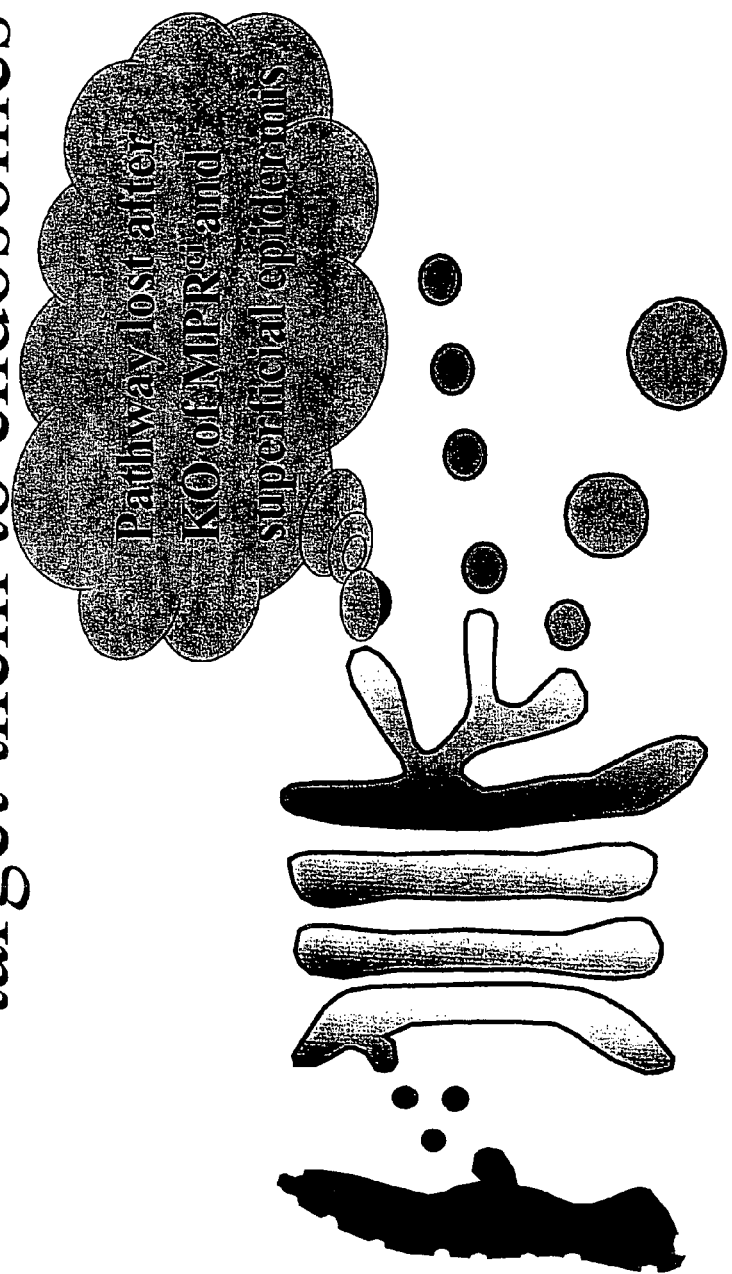
FIG. 2 illustrates that mannose-6-phosphate receptors (MPRs) sort lysosomal enzymes and target them to endosomes.
Figure 3:
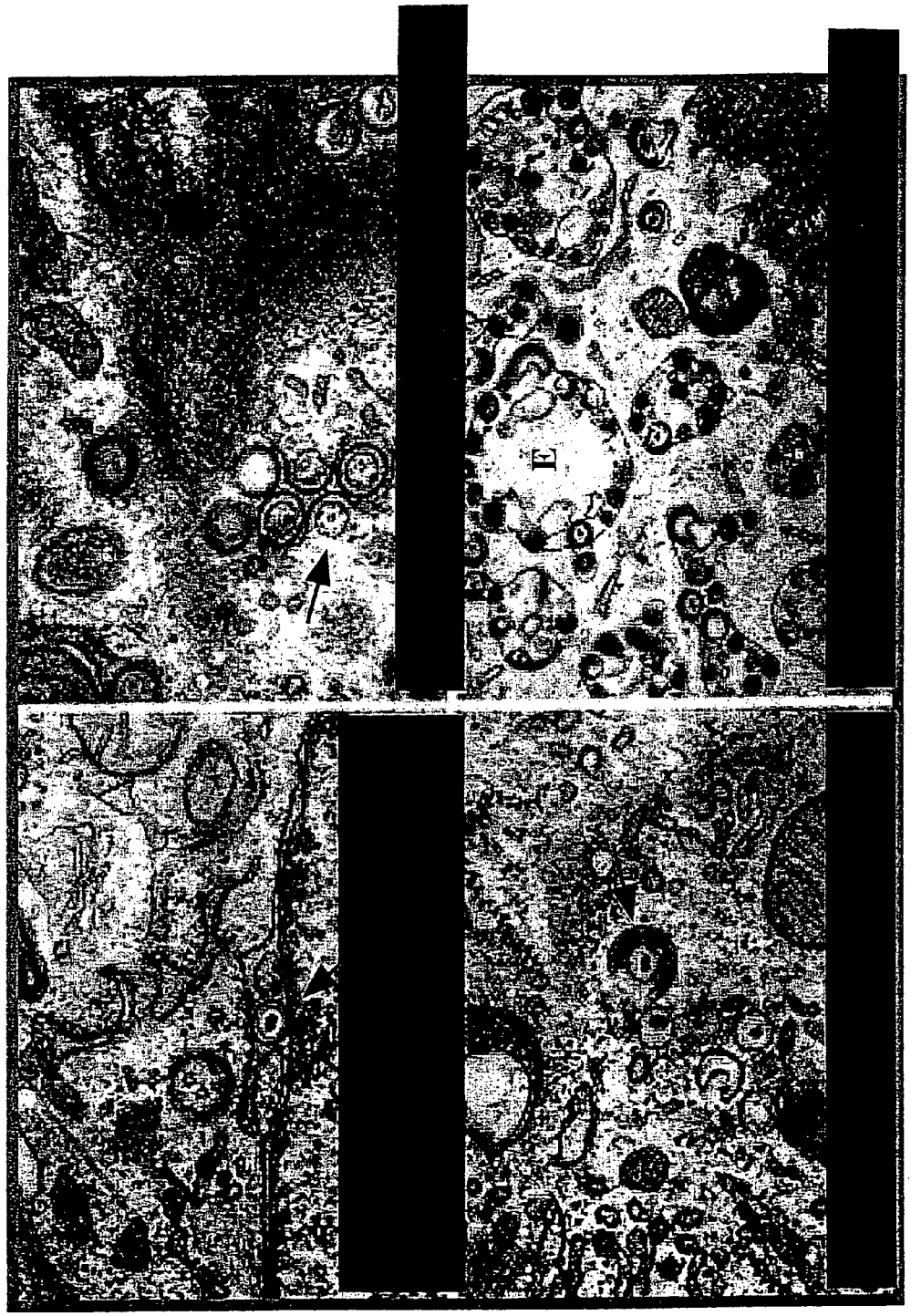
FIG. 3 illustrates intracellular transport of VZV and packing of the final envelope in the trans-Golgi network (TGN)
Figure 5:
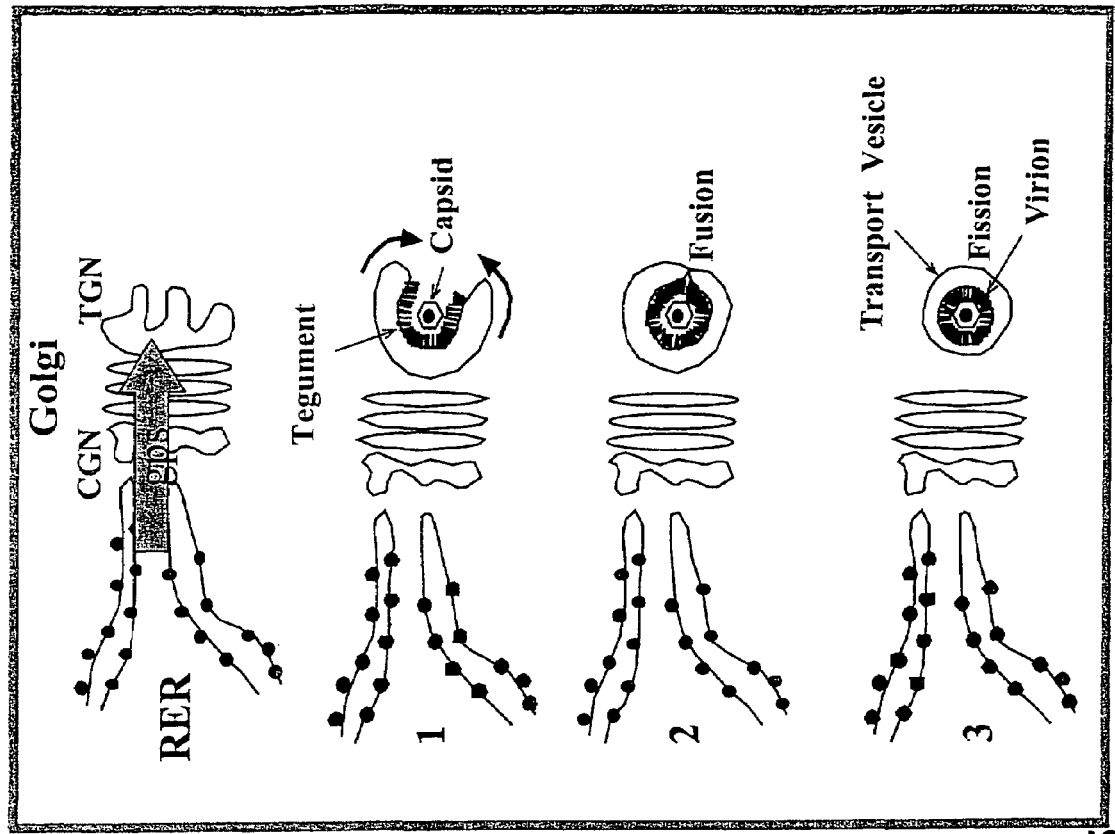
FIG. 5 illustrates the mechanism by which VZV particles receive their final envelope in the TGN.
Figure 7:
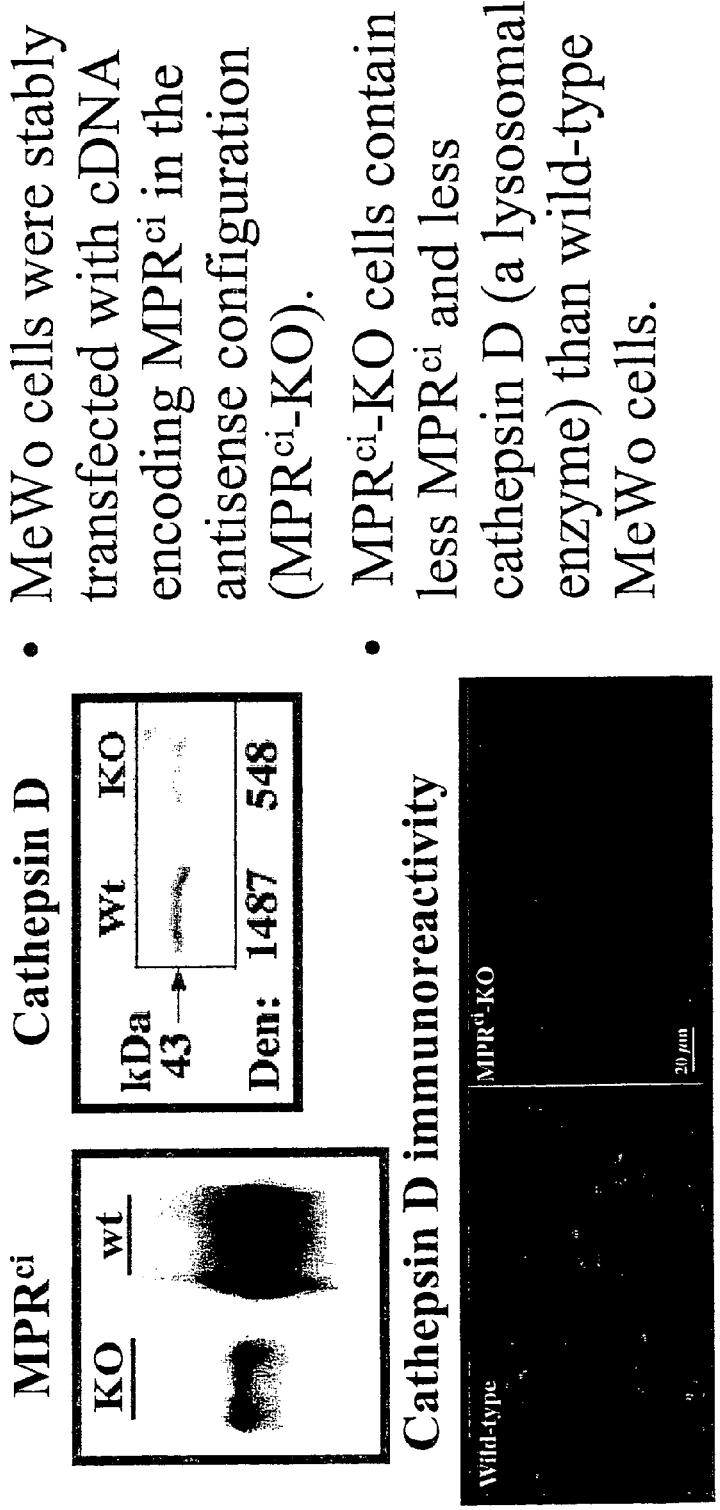
FIG. 7 demonstrates that expression of cation-independent MPRs ($MPR^{ci}$s) in MeWo cells is downregulated by antisense cDNA;W
Figure 14:
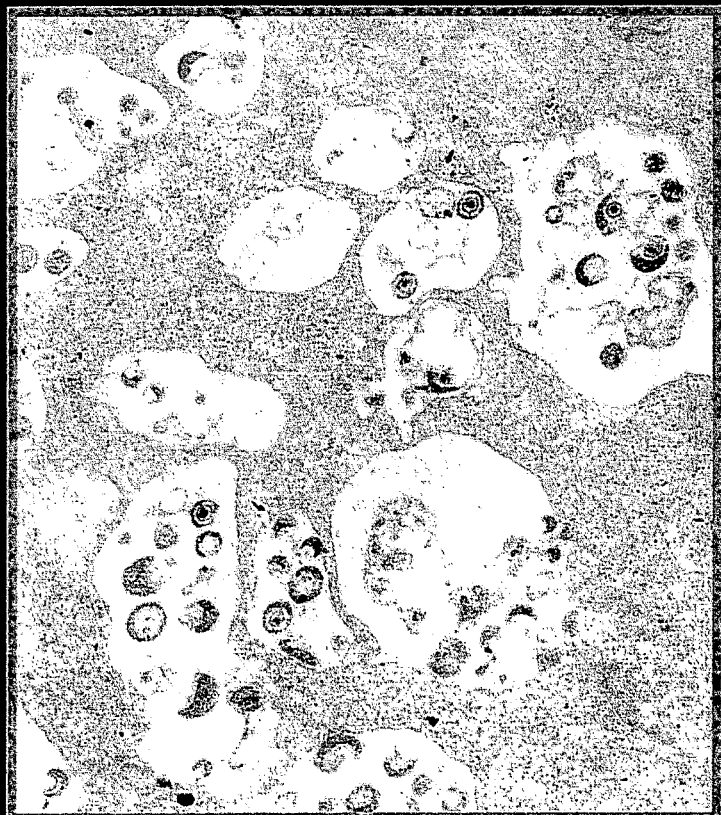
FIG. 14 demonstrates that VZV accumulates in late endosomes in parental MeWo cells.
Figure 15:
FIG. 15 illustrates that enveloped VZV is released intact in the superficial epidermis.

The foregoing results are summarized in FIGS. 1-15. The data confirm that the Man 6-P/IGF2R-deficient MeWo cells have a reduced ability to divert lysosomal enzymes from their secretory pathway to endosomes.

Example 2

Development of Animal Model of VZV Latency

VZV has a narrow host range. However, it is known to be neurotropic, and to become latent in sensory ganglia. Because the enteric nervous system (ENS) contains intrinsic sensory neurons, the inventors postulated that VZV may infect, and become latent in, the ENS (e.g., enteric neurons and/or enteric ganglia).

The ENS is an independent autonomic division that is capable of regulating the behavior of the gut without input from the central nervous system (CNS). The ENS has independence from the CNS because it contains two main types of intrinsic primary afferent neurons (IPANS): submucosal IPANS (containing cholinergic-CGRP or substance-P) or myenteric IPANS (containing cholinergic calbindin). The inventors found that reactivation of VZV in enteric neurons could provide a source of visceral zoster, and present a model for understanding the origin of zoster. This was established by first testing the ability of VZV to establish latency in guinea pig enteric ganglia in vitro, and then by testing the ability of the latent VZV to reactivate.

The inventors first isolated ganglia from guinea pig small intestine. The LM-MP was mechanically dissected from the bowel, and dissociated with collagenase. Myenteric ganglia then were individually selected and cultured. Mitotic inhibitors were used to decrease growth of non-neuronal cells, enabling enteric neurons to reorganize and interconnect. Cell-free VZV was adsorbed for 4 h, approximately 5 days after the ganglia were plated. Cultures were maintained for 4-6 weeks thereafter.

Figure 16:
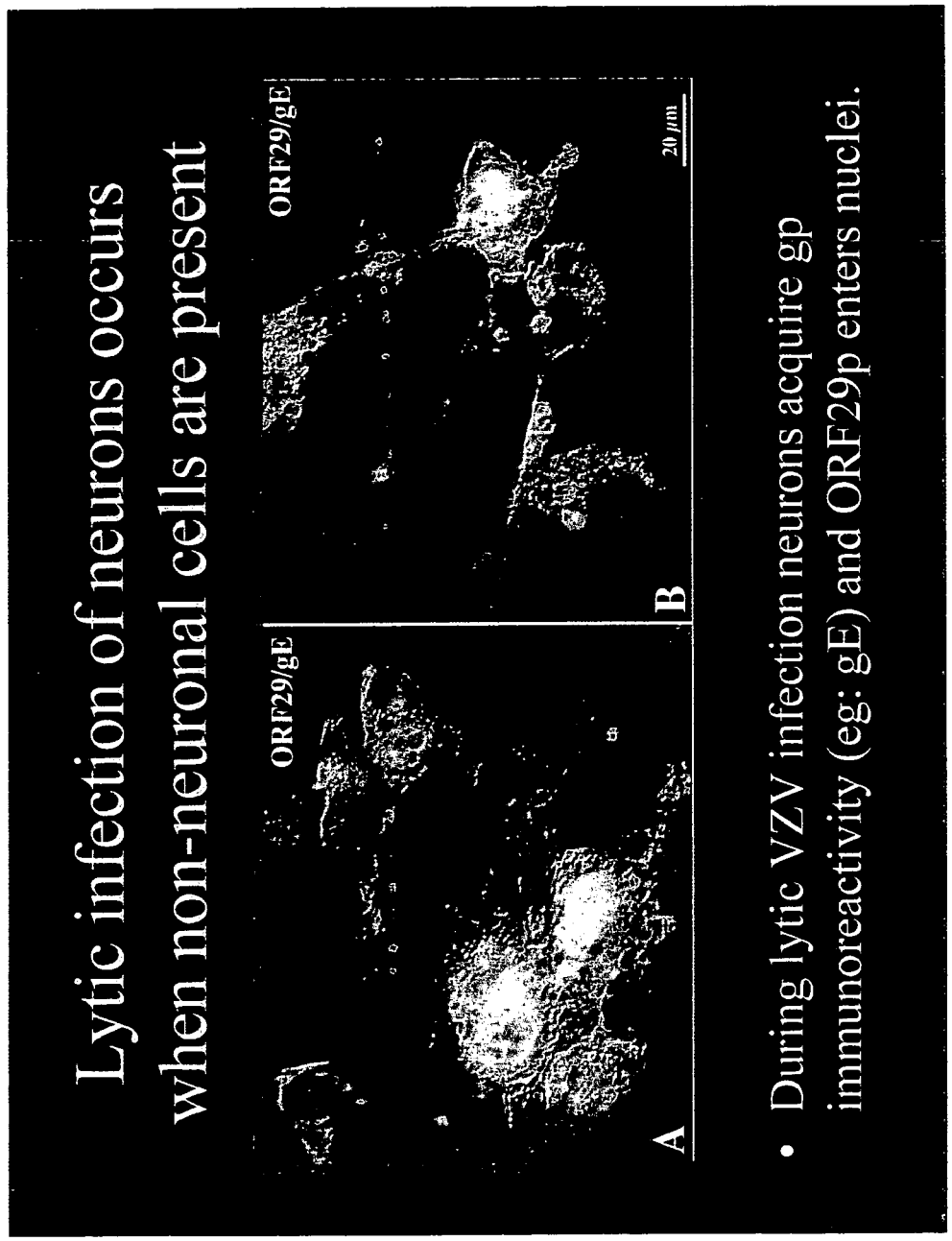
FIG. 16 shows that lytic infection of neurons occurs when non-neuronal cells are present.
Figure 17:
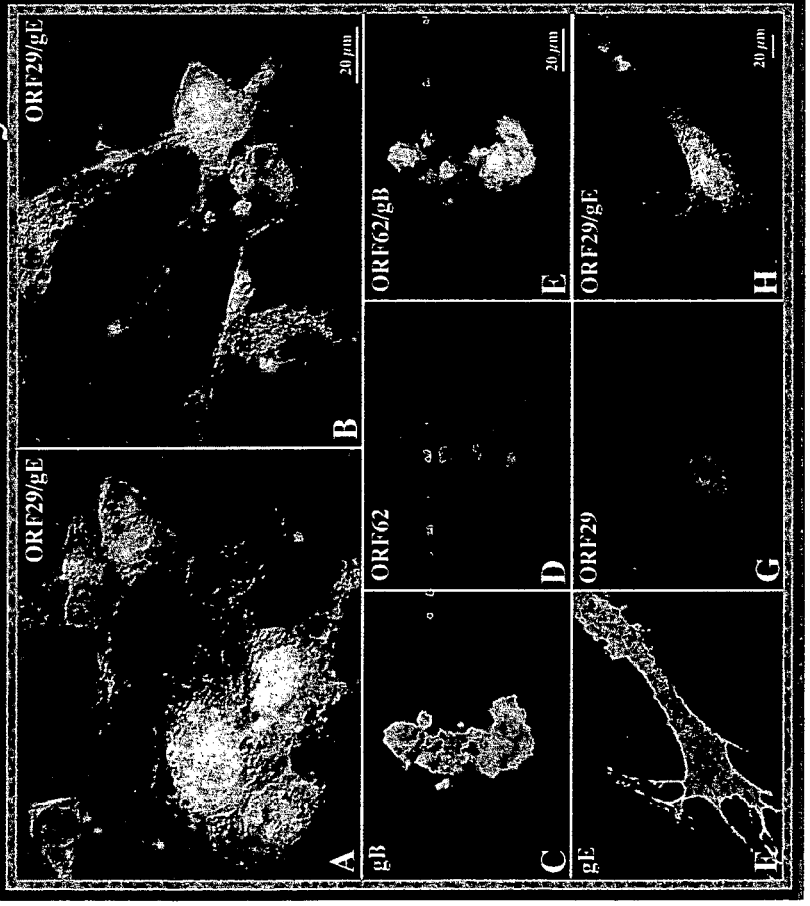
FIG. 17 illustrates that neurons die within two days when infection is lytic.
Figure 19:
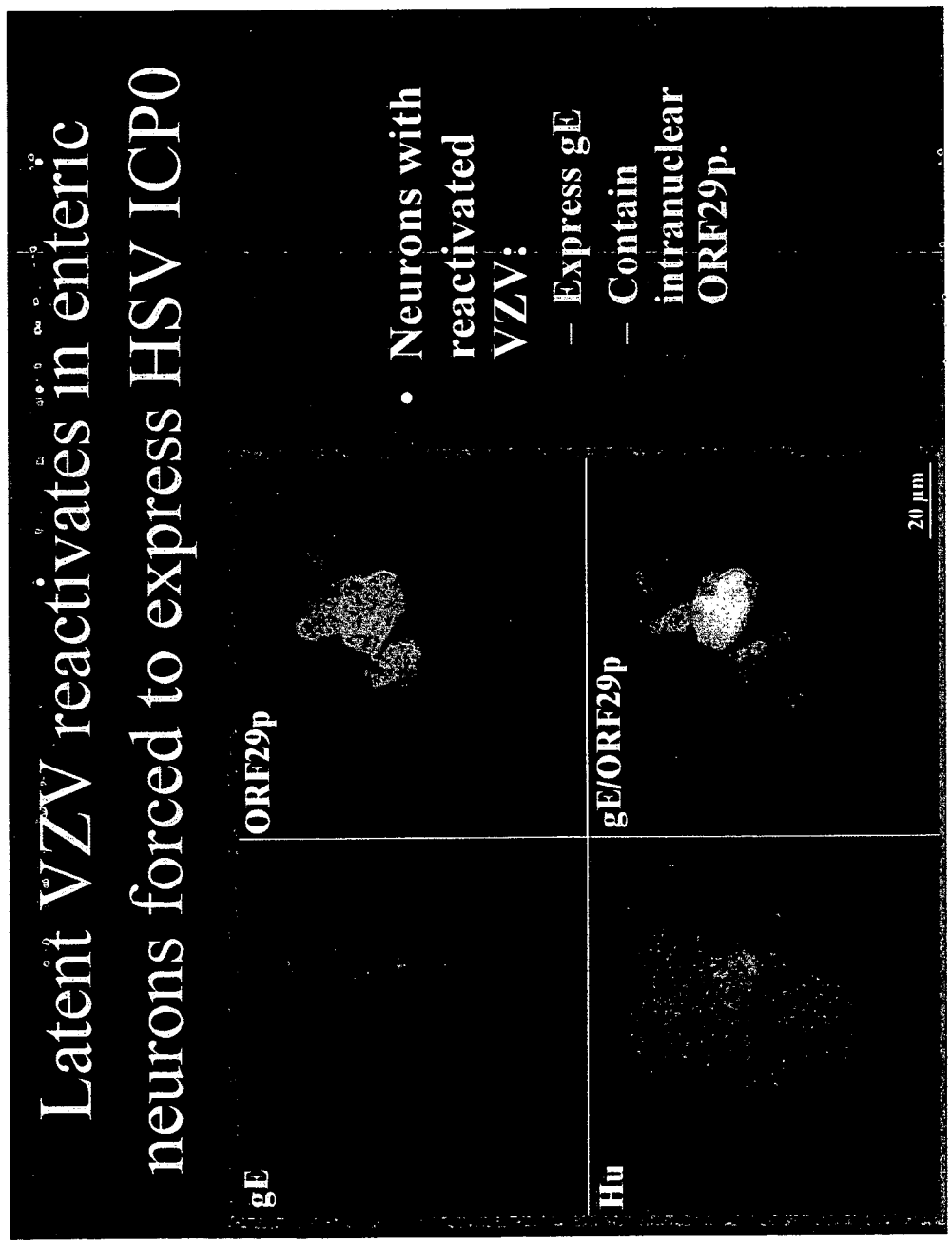
FIG. 19 shows that latent VZV reactivates in enteric neurons forced to express HSV ICP0.
Figure 20:
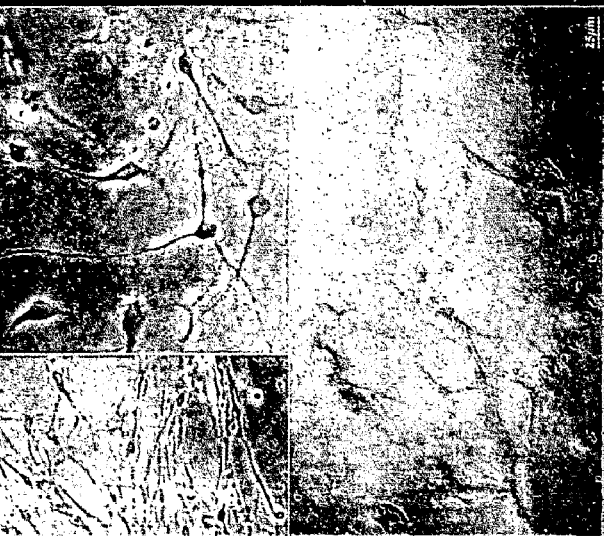
FIG. 20 shows that cultured ganglia contain few non-neuronal cells.
Figure 21:
FIG. 21 demonstrates that RT-PCR reveals expression of VZV DNA and RNA in isolated ganglia.
Figure 23:
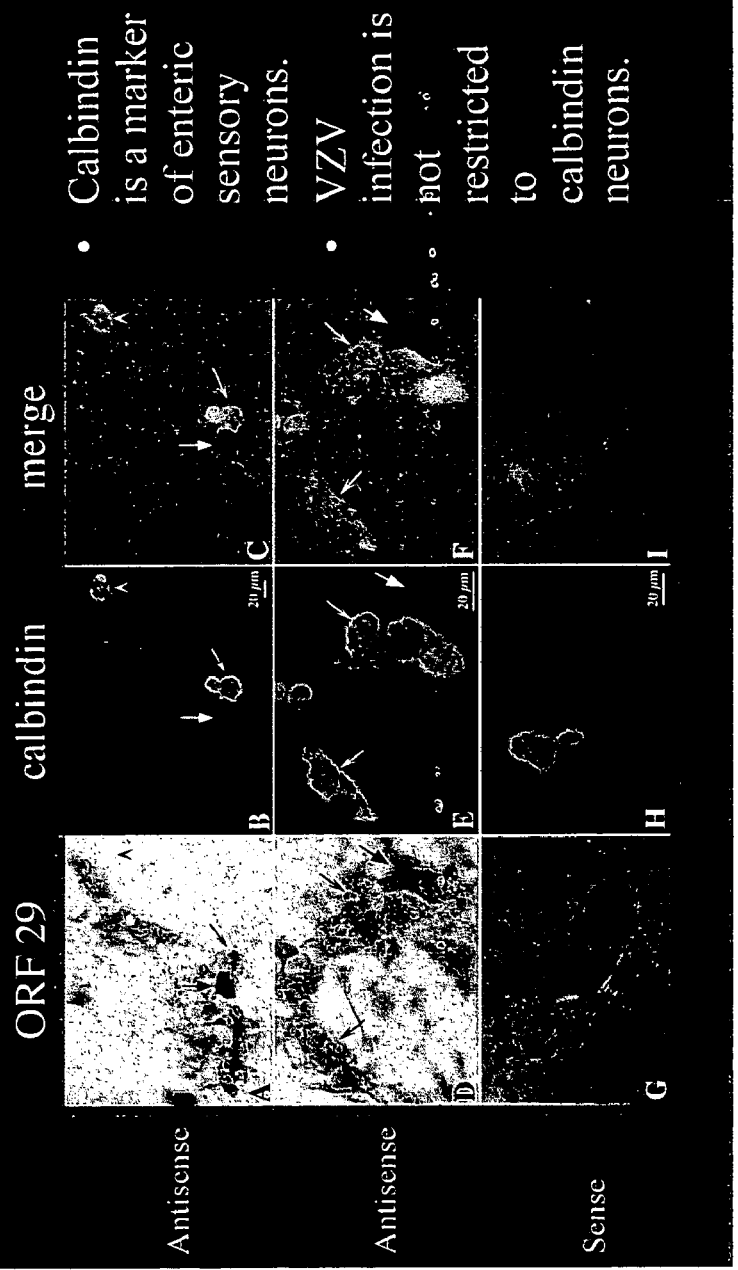
FIG. 23 illustrates that ORF29 mRNA is found by in situ hybridization in subsets of neurons.
Figure 24:
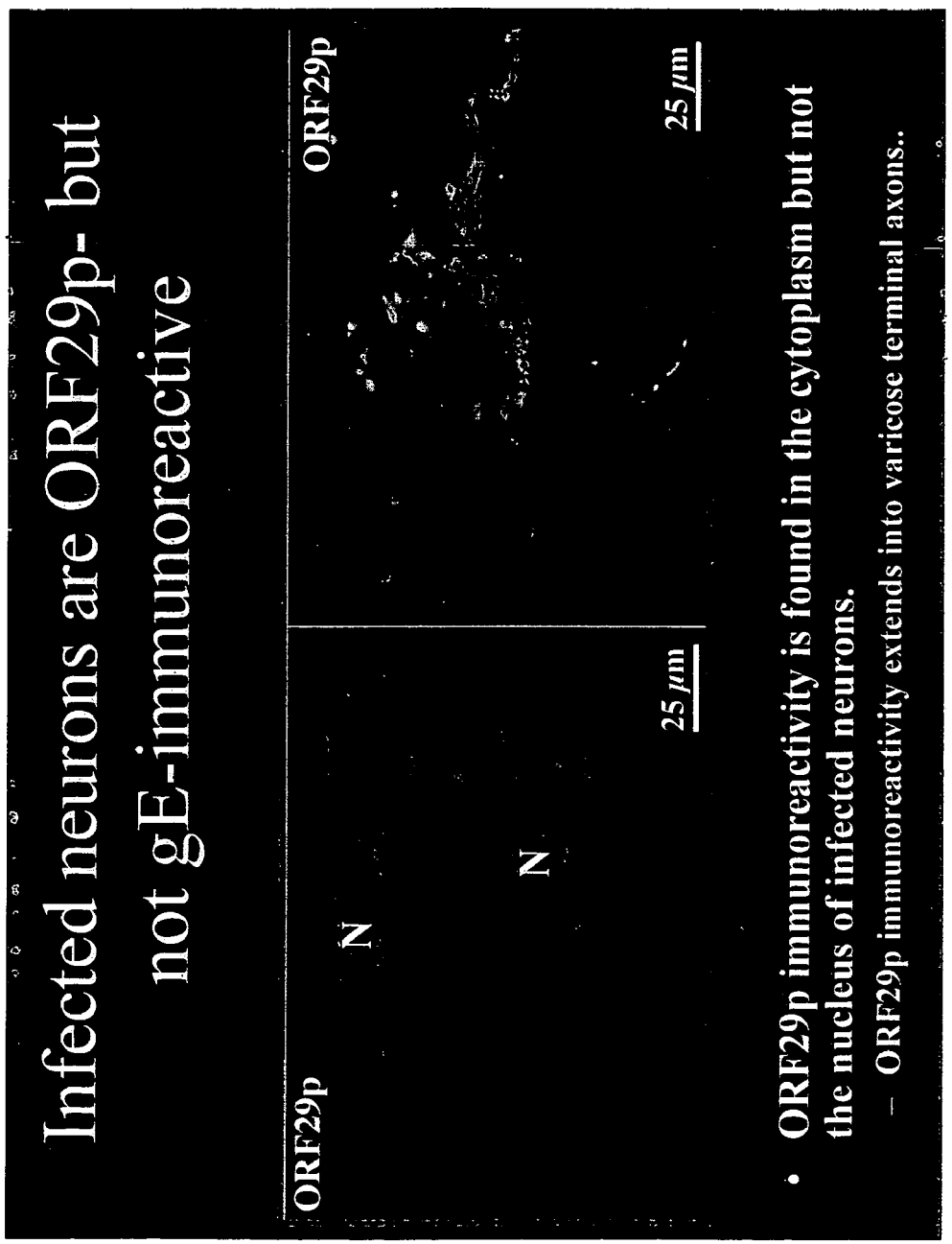
FIG. 24 demonstrates that infected neurons are ORF29p- but not gE-immunoreactive.
Figure 25:
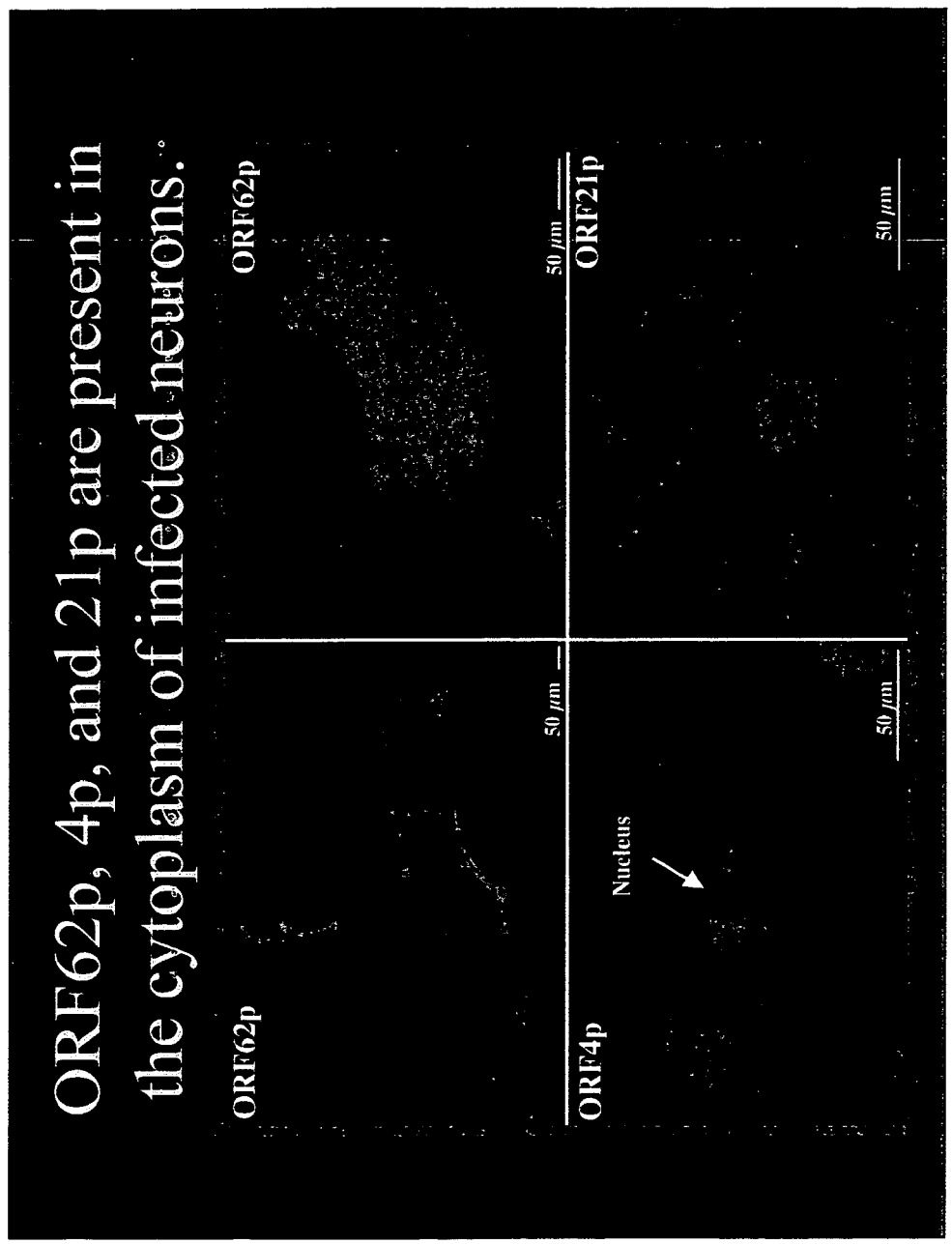
FIG. 25 shows that ORF62p, 4p, and 21p are present in the cytoplasm of infected neurons.

As shown in FIGS. 16-25, VZV infected guinea pig enteric ganglia in vitro. Latent infection occurred with the use of cultures highly enriched in neurons. It was observed that neurons expressed only those VZV proteins that had been reported to be expressed during VZV latency in human sensory ganglia (no glycoproteins). In this regard, it is noted that ORF62p and ORF29p are cytoplasmic, not nuclear. Lytic infection required the presence of non-neuronal cells. Both neurons and non-neuronal cells expressed glycoproteins, and ORF62p and ORF29p were found in nuclei. Reactivation occurred in neurons, and likely occurred in glia. Reactivation was induced by expression of HSV ICP0 (the HSV homologue of VZV ORF61). Neurons expressed glycoproteins, and ORF29p was found in nuclei. The model of the in vitro reactivation of VZV described herein is the first in vitro model for shingles.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A genetically engineered cell line stably transformed with a nucleotide sequence encoding at least two full-length mannose-6-phosphate receptors in the antisense configuration.

2. A genetically engineered cell line stably transformed with nucleotide sequence encoding a full-length cation dependent mannose-6-phosphate receptor in the antisense configuration and a full-length cation independent mannose-6-phosphate receptor/insulin-like growth factor receptor (Man-6P/IGF2R) in the antisense configuration.

3. A recombinant vector comprising a nucleotide sequence encoding at least two full-length mannose-6-phosphate receptors in the antisense configuration.

* * * * *

UNITED STATES PATENT AND TRADEMARK OFFICE
CERTIFICATE OF CORRECTION

| | | |
|---|---|---|
| PATENT NO. | : 7,273,616 B2 | Page 1 of 1 |
| APPLICATION NO. | : 10/436706 | |
| DATED | : September 25, 2007 | |
| INVENTOR(S) | : Jason J. Chen et al. | |

It is certified that error appears in the above-identified patent and that said Letters Patent is hereby corrected as shown below:

In the Specification:

In column 1, Line 12 please insert the following:

--STATEMENT OF GOVERNMENT INTEREST

This invention was made with government support under AI027187 awarded by National Institute of Health. The government has certain rights in the invention.--

Signed and Sealed this
Thirtieth Day of April, 2013

Teresa Stanek Rea
*Acting Director of the United States Patent and Trademark Office*

SEQUENCE LISTING

```
<160> NUMBER OF SEQ ID NOS: 2

<210> SEQ ID NO 1
<211> LENGTH: 834
<212> TYPE: DNA
<213> ORGANISM: Homo sapiens

<400> SEQUENCE: 1 atgttcccttt tctacagctg ctggaggact ggactgctac tactactcct ggctgtggca      60
gtgagagaat cctggcagac agaagaaaaa acttgcgact tggtaggaga aagggtaaa      120 gagtcagaga aagagttggc tctagtgaag aggctgaaac cactgtttaa taaaagcttt      180
gagagcactg tgggccaggg ttcagacaca tacatctaca tcttcagggt gtgccgggaa      240
```

-continued

```
gctggcaacc acacttctgg ggcaggcctg gtgcaaatca acaaaagtaa tgggaaggag     300
acagtggtag ggagactcaa cgagactcac atcttcaacg gaagtaattg gatcatgctg     360
atctataaag gggtgatgaa atatgacaac cactgtggca aggagcagcg tcgtgcagtg     420
gtgatgatct cctgcaatcg acacacccta gcggacaatt ttaaccctgt gtctgaggag     480
cgtggcaaag tccaagattg tttctacctc tttgagatgg atagcagcct ggcctgttca     540
ccagagatct cccacctcag tgtgggttcc atcttacttg tcacgtttgc atcactggtt     600
gctgtttatg ttgttggggg gttcctatac cagcgactgg tagtgggagc caaaggaatg     660
gagcagtttc cccacttagc cttctggcag gatcttggca acctggtagc agatggctgt     720
gactttgtct gccgttctaa acctcgaaat gtgcctgcag catatcgtgg tgtgggggat     780
gaccagctgg gggaggagtc agaagaaagg gatgaccatt tattaccaat gtag         834
```

<210> SEQ ID NO 2
<211> LENGTH: 7476
<212> TYPE: DNA
<213> ORGANISM: Homo sapiens
<400> SEQUENCE: 2

```
atggggccg ccgccggccg gagccccac ctggggcccg cgcccgcccg ccgcccgcag      60
cgctctctgc tcctgctgca gctgctgctg ctcgtcgctg ccccggggtc cacgcaggcc    120
caggccgccc cgttccccga gctgtgcagt tatacatggg aagctgttga taccaaaaat    180
aatgtacttt ataaaatcaa catctgtgga agtgtggata ttgtccagtg cgggccatca    240
agtgctgttt gtatgcacga cttgaagaca cgcacttatc attcagtggg tgactctgtt    300
ttgagaagtg caaccagatc tctcctggaa ttcaacacaa cagtgagctg tgaccagcaa    360
ggcacaaatc acagagtcca gagcagcatt gccttcctgt gtgggaaaac cctgggaact    420
cctgaatttg taactgcaac agaatgtgtg cactactttg agtggaggac cactgcagcc    480
tgcaagaaag acatatttaa agcaaataag gaggtgccat gctatgtgtt tgatgaagag    540
ttgaggaagc atgatctcaa tcctctgatc aagcttagtg gtgcctactt ggtggatgac    600
tccgatccgg acacttctct attcatcaat gtttgtagag acatagacac actacgagac    660
ccaggttcac agctgcgggc ctgtcccccc ggcactgccg cctgcctggt aagaggacac    720
caggcgtttg atgttggcca gccccgggac ggactgaagc tggtgcgcaa ggacaggctt    780
gtcctgagtt acgtgaggga agaggcagga aagctagact tttgtgatgg tcacagcccct   840 gcggtgacta ttacatttgt ttgcccgtcg gagcggagag agggcaccat tcccaaactc    900
acagctaaat ccaactgccg ctatgaaatt gagtggatta ctgagtatgc ctgccacaga    960
gattacctgg aaagtaaaac ttgttctctg agcggcgagc agcaggatgt ctccatagac   1020
ctcacaccac ttgcccagag cggaggttca tcctatattt cagatggaaa agaatatttg   1080 tttatttga atgtctgtgg agaaactgaa atacagttct gtaataaaaa acaagctgca   1140
gtttgccaag tgaaaagag cgatacctct caagtcaaag cagcaggaag ataccacaat   1200
cagaccctcc gatattcgga tggagacctc accttgatat attttggagg tgatgaatgc   1260
agctcagggt tcagcggat gagcgtcata actttgagt gcaataaaac cgcaggtaac   1320
gatgggaaag gaactcctgt attcacaggg gaggttgact gcacctactt cttcacatgg   1380 gacacgggaat acgcctgtgt taaggagaag gaagacctcc tctgcggtgc caccgacggg   1440
aagaagcgct atgacctgtc cgcgctggtc cgccatgcag aaccagagca gaattgggaa   1500
```

-continued

```
gctgtggatg gcagtcagac ggaaacagag aagaagcatt ttttcattaa tatttgtcac    1560
agagtgctgc aggaaggcaa ggcacgaggg tgtcccgagg acgcggcagt gtgtgcagtg    1620
gataaaaatg gaagtaaaaa tctgggaaaa tttatttcct ctcccatgaa agagaaagga    1680
aacattcaac tctcttattc agatggtgat gattgtggtc atggcaagaa aattaaaact    1740
aatatcacac ttgtatgcaa gccaggtgat ctggaaagtg caccagtgtt gagaacttct    1800
ggggaaggcg gttgctttta tgagtttgag tggcacacac ctgcggcctg tgtgctgtct    1860
aagacagaag gggagaactg cacggtcttt gactcccagg cagggttttc ttttgactta    1920
tcacctctca caaagaaaaa tggtgcctat aaagttgaga caaagaagta tgacttttat    1980
ataaatgtgt gtggcccggt gtctgtgagc ccctgtcagc cagactcagg agcctgccag    2040
gtggcaaaaa gtgatgagaa acttggaac ttgggtctga gtaatgcgaa gctttcatat    2100
tatgatggga tgatccaact gaactacaga ggcggcacac cctataacaa tgaaagacac    2160
acaccgagag ctacgctcat cacctttctc tgtgatcgag acgcgggagt gggcttccct    2220
gaatatcagg aagaggataa ctccacctac aacttccggt ggtacaccag ctatgcctgc    2280
ccggaggagc ccctgaatg cgtagtgacc gaccctcca cgctggagca gtacgacctc    2340
tccagtctgg caaaatctga aggtggcctt ggaggaaact ggtatgccat ggacaactca    2400
ggggaacatg tcacgtggag gaaatactac attaacgtgt gtcggcctct gaatccagtg    2460
ccgggctgca accgatatgc atcggcttgc cagatgaagt atgaaaaaga tcagggctcc    2520
ttcactgaag tggttttccat cagtaacttg ggaatggcaa agaccggccc ggtggttgag    2580
gacagcggca gcctccttct ggaatacgtg aatgggtcgg cctgcaccac cagcgatggc    2640
agacagacca catataccac gaggatccat ctcgtctgct ccaggggcag gctgaacagc    2700
caccccatct tttctctcaa ctgggagtgt gtggtcagtt tcctgtggaa cacagaggct    2760
gcctgtccca ttcagacaac gacggataca gaccaggctt gctctataag ggatcccaac    2820
agtggatttg tgtttaatct taatccgcta aacagttcgc aaggatataa cgtctctggc    2880
attgggaaga ttttttatgtt taatgtctgc ggcacaatgc ctgtctgtgg gaccatcctg    2940
ggaaaacctg cttctggctg tgaggcagaa acccaaactg aagagctcaa gaattggaag    3000
ccagcaaggc cagtcggaat tgagaaaagc ctccagctgt ccacagaggg cttcatcact    3060
ctgacctaca agggcctct ctctgccaaa ggtaccgctg atgcttttat cgtccgcttt    3120
gtttgcaatg atgatgttta ctcagggccc ctcaaattcc tgcatcaaga tatcgactct    3180
gggcaaggga tccgaaacac ttactttgag tttgaaaccg cgttggcctg tgttccttct    3240
ccagtggact gccaagtcac cgacctggct ggaaatgagt acgacctgac tggcctaagc    3300
acagtcagga aaccttggac ggctgttgac acctctgtcg atgggagaaa gaggactttc    3360
tatttgagcg tttgcaatcc tctcccttac attcctggat gccagggcag cgcagtgggg    3420
tcttgcttag tgtcagaagg caatagctgg aatctgggtg tggtgcagat gagtccccaa    3480
gccgcggcga atggatcttt gagcatcatg tatgtcaacg gtgacaagtg tgggaaccag    3540
cgcttctcca ccaggatcac gtttgagtgt gctcagatat cgggctcacc agcatttcag    3600
cttcaggatg gttgtgagta cgtgtttatc tggagaactg tggaagcctg tcccgttgtc    3660
agagtggaag gggacaactg tgaggtgaaa gacccaaggc atggcaactt gtatgacctg    3720
aagcccctgg gcctcaacga caccatcgtg agcgctggcg aatacactta ttacttccgg    3780
gtctgtggga agctttcctc agacgtctgc cccacaagtg acaagtccaa ggtggtctcc    3840
tcatgtcagg aaaagcggga accgcaggga tttcacaaag tggcaggtct cctgactcag    3900
```

-continued

| | |
|---|---|
| aagctaactt atgaaaatgg cttgttaaaa atgaacttca cggggggggga cacttgccat | 3960 |
| aaggtttatc agcgctccac agccatcttc ttctactgtg accgcggcac ccagcggcca | 4020 |
| gtatttctaa aggagacttc agattgttcc tacttgtttg agtggcgaac gcagtatgcc | 4080 |
| tgcccacctt tcgatctgac tgaatgttca ttcaaagatg gggctggcaa ctccttcgac | 4140 |
| ctctcgtccc tgtcaaggta cagtgacaac tgggaagcca tcactgggac ggggacccg | 4200 |
| gagcactacc tcatcaatgt ctgcaagtct ctggcccgc aggctggcac tgagccgtgc | 4260 |
| cctccagaag cagccgcgtg tctgctgggt ggctccaagc ccgtgaacct cggcagggta | 4320 |
| agggacggac ctcagtggag agatggcata attgtcctga aatacgttga tggcgactta | 4380 |
| tgtccagatg ggattcggaa aaagtcaacc accatccgat tcacctgcag cgagagccaa | 4440 |
| gtgaactcca ggcccatgtt catcagcgcc gtggaggact gtgagtacac ctttgcctgg | 4500 |
| cccacagcca cagcctgtcc catgaagagc aacgagcatg atgactgcca ggtcaccaac | 4560 |
| ccaagcacag gacacctgtt tgatctgagc tccttaagtg gcagggcggg attcacagct | 4620 |
| gcttacagcg agaaggggtt ggtttacatg agcatctgtg gggagaatga aaactgccct | 4680 |
| cctggcgtgg gggcctgctt tggacagacc aggattagcg tgggcaaggc caacaagagg | 4740 |
| ctgagatacg tggaccaggt cctgcagctg gtgtacaagg atgggtcccc ttgtccctcc | 4800 |
| aaatccggcc tgagctataa gagtgtgatc agtttcgtgt gcaggcctga ggccgggcca | 4860 |
| accaataggc ccatgctcat ctccctggac aagcagacat gcactctctt cttctcctgg | 4920 |
| cacacgccgc tggcctgcga gcaagcgacc gaatgttccg tgaggaatgg aagctctatt | 4980 |
| gttgacttgt ctccccttat tcatcgcact ggtggttatg aggcttatga tgagagtgag | 5040 |
| gatgatgcct ccgataccaa ccctgatttc tacatcaata tttgtcagcc actaaatccc | 5100 |
| atgcacggag tgccctgtcc tgccggagcc gctgtgtgca agttcctat tgatggtccc | 5160 |
| cccatagata tcggccgggt agcaggacca ccaatactca atccaatagc aaatgagatt | 5220 |
| tacttgaatt ttgaaagcag tactccttgc ttagcggaca agcatttcaa ctacacctcg | 5280 |
| ctcatcgcgt ttcactgtaa gagaggtgtg agcatgggaa cgcctaagct gttaaggacc | 5340 |
| agcgagtgcg actttgtgtt cgaatgggag actcctgtcg tctgtcctga tgaagtgagg | 5400 |
| atggatggct gtaccctgac agatgagcag ctcctctaca gcttcaactt gtccagcctt | 5460 |
| tccacgagca cctttaaggt gactcgcgac tcgcgcacct acagcgttgg ggtgtgcacc | 5520 |
| tttgcagtcg ggccagaaca aggaggctgt aaggacggag gagtctgtct gctctcaggc | 5580 |
| accaagggg catcctttgg acggctgcaa tcaatgaaac tggattacag gcaccaggat | 5640 |
| gaagcggtcg ttttaagtta cgtgaatggt gatcgttgcc ctccagaaac cgatgacggc | 5700 |
| gtcccctgtg tcttcccctt catattcaat gggaagagct acgaggagtg catcatagag | 5760 |
| agcagggcga agctgtggtg tagcacaact gcggactacg acagagacca cgagtggggc | 5820 |
| ttctgcagac actcaaacag ctaccggaca tccagcatca tatttaagtg tgatgaagat | 5880 |
| gaggacattg ggaggccaca agtcttcagt gaagtgcgtg ggtgtgatgt gacatttgag | 5940 |
| tggaaaacaa aagttgtctg ccctccaaag aagttggagt gcaaattcgt ccagaaacac | 6000 |
| aaaacctacg acctgcggct gctctcctct ctcaccgggt cctggtccct ggtccacaac | 6060 |
| ggagtctcgt actatataaa tctgtgccag aaaatatata agggcccct gggctgctct | 6120 |
| gaaagggcca gcatttgcag aaggaccaca actggtgacg tccaggtcct gggactcgtt | 6180 |
| cacacgcaga agctgggtgt cataggtgac aaagttgttg tcacgtactc caaaggttat | 6240 |

-continued

```
ccgtgtggtg gaaataagac cgcatcctcc gtgatagaat tgacctgtac aaagacggtg    6300
ggcagacctg cattcaagag gtttgatatc gacagctgca cttactactt cagctgggac    6360
tcccgggctg cctgcgccgt gaagcctcag gaggtgcaga tggtgaatgg gaccatcacc    6420
aaccctataa atggcaagag cttcagcctc ggagatattt attttaagct gttcagagcc    6480
tctggggaca tgaggaccaa tggggacaac tacctgtatg agatccaact ttcctccatc    6540
acaagctcca gaaacccggc gtgctctgga gccaacatat gccaggtgaa gcccaacgat    6600
cagcacttca gtcggaaagt tggaacctct gacaagacca agtactacct tcaagacggc    6660
gatctcgatg tcgtgtttgc ctcttcctct aagtgcggaa aggataagac caagtctgtt    6720
tcttccacca tcttcttcca ctgtgaccct ctggtggagg acgggatccc cgagttcagt    6780
cacgagactg ccgactgcca gtacctcttc tcttggtaca cctcagccgt gtgtcctctg    6840
ggggtgggct ttgacagcga gaatcccggg gacgacgggc agatgcacaa ggggctgtca    6900
gaacggagcc aggcagtcgg cgcggtgctc agcctgctgc tggtggcgct cacctgctgc    6960
ctgctggccc tgttgctcta caagaaggag aggagggaaa cagtgataag taagctgacc    7020
acttgctgta ggagaagttc caacgtgtcc tacaaatact caaaggtgaa taaggaagaa    7080
gagacagatg agaatgaaac agagtggctg atggaagaga tccagctgcc tcctccacgg    7140
cagggaaagg aagggcagga gaacggccat attaccacca agtcagtgaa agccctcagc    7200
tccctgcatg gggatgacca ggacagtgag gatgaggttc tgaccatccc agaggtgaaa    7260
gttcactcgg gcaggggagc tggggcagag agctcccacc cagtgagaaa cgcacagagc    7320
aatgcccttc aggagcgtga ggacgatagg gtggggctgg tcagggtga gaaggcgagg    7380 aaagggaagt ccagctctgc acagcagaag acagtgagct ccaccaagct ggtgtccttc    7440
catgacgaca gcgacgagga cctcttacac atctga                              7476
```